(12) United States Patent
Christiano et al.

(10) Patent No.: US 10,155,839 B2
(45) Date of Patent: Dec. 18, 2018

(54) ADDUCT OF AN AMINE AND A CYCLIC SILOXANE COMPOUND

(71) Applicant: Milliken & Company, Spartanburg, SC (US)

(72) Inventors: Steven P. Christiano, Spartanburg, SC (US); Olha V. Hoy, Greenville, SC (US); Robbie W. J. M. Hanssen, Boiling Springs, SC (US)

(73) Assignee: Milliken & Company, Spartanburg, SC (US)

(*) Notice: Subject to any disclaimer, the term of this patent is extended or adjusted under 35 U.S.C. 154(b) by 0 days.

(21) Appl. No.: 15/348,151

(22) Filed: Nov. 10, 2016

(65) Prior Publication Data
US 2017/0145149 A1    May 25, 2017

Related U.S. Application Data

(60) Provisional application No. 62/257,471, filed on Nov. 19, 2015.

(51) Int. Cl.
*C08G 59/14* (2006.01)
*C08G 77/38* (2006.01)
*C07F 7/21* (2006.01)

(52) U.S. Cl.
CPC ............ *C08G 59/1477* (2013.01); *C07F 7/21* (2013.01); *C08G 77/38* (2013.01)

(58) Field of Classification Search
CPC ........... C07F 7/21; C08G 77/26; C08G 77/80; C08L 63/00; C08L 63/04
USPC .............................................. 528/28, 37, 43
See application file for complete search history.

(56) References Cited

U.S. PATENT DOCUMENTS

| | | | |
|---|---|---|---|
| 3,455,877 A | 7/1969 | Plueddemann | |
| 4,208,503 A | 6/1980 | Martin | |
| 4,245,079 A | 1/1981 | Natsumoto et al. | |
| 4,892,918 A | 1/1990 | Ryang | |
| 4,944,989 A | 7/1990 | Dorsch et al. | |
| 5,037,861 A | 8/1991 | Crivello et al. | |
| 5,153,332 A | 10/1992 | Enami et al. | |
| 5,359,109 A | 10/1994 | Ritscher et al. | |
| 5,378,790 A | 1/1995 | Michalczyk et al. | |
| 5,523,374 A * | 6/1996 | Bard | C08G 77/50 528/26 |
| 6,005,131 A | 12/1999 | Jentsch et al. | |
| 6,030,919 A | 2/2000 | Lewis | |
| 6,624,236 B1 | 9/2003 | Bissinger et al. | |
| 7,777,064 B2 * | 8/2010 | Mizori | C09J 5/00 556/439 |
| 8,008,419 B2 | 8/2011 | Dershem | |
| 8,415,812 B2 | 4/2013 | Dershem et al. | |
| 8,431,655 B2 | 4/2013 | Bershem | |
| 8,513,375 B2 | 8/2013 | Mizori et al. | |
| 8,541,531 B2 | 9/2013 | Dershem | |
| 8,580,888 B2 | 11/2013 | Tully et al. | |
| 9,006,307 B2 * | 4/2015 | Iezzi | C09D 163/00 523/150 |
| 9,073,950 B2 | 7/2015 | Kownacka et al. | |
| 2010/0041823 A1 | 2/2010 | Dershem | |
| 2013/0228901 A1 | 9/2013 | Dershem et al. | |

FOREIGN PATENT DOCUMENTS

| | | |
|---|---|---|
| CN | 102634027 A | 8/2012 |
| EP | 1 207 163 A2 | 5/2002 |
| WO | WO 2012/035112 A1 | 3/2012 |

OTHER PUBLICATIONS

International Search Report PCT/US2016/061276, filed Nov. 10, 2016, 4 pages.
Written Opinion of the International Searching Authority PCT/US2016/061276, filed Nov. 10, 2016, 5 pages.
Wang Hongwei et al., "*Chromatographic Assessment of Two Hybrid Monoliths Preparedviaepoxy-amine Ring-Opening Polymerization and Methacrylate-based Free Radical Polymerization Using Methacrylate Epoxy Cyclosiloxane as Functional Monomer.*" Journal of chromatography A, Elsevier, Amsterdam, NL. vol. 1367, pp. 131-140.
Baej Gierczyk et al., "*New Polymeric Metal Ion Scavengers with Polyamine Podand Moieties,*"Reactive and Functional Polymers, Elsevier, Amsterdam, NL. vol. 71, No. 4, pp. 463-479.
Omari Mukbaniani et al., "*Siloxane Oligomers with Epoxy Pendant Groups,*" Macromolecular Symposia., vol. 328 , No. 1. pp. 25-37.
Khananashvili, L.M. et al., Synthesis of Epoxycontaining Siliconorganic Compounds. Intern. J. Polymeric Mater., 1995, vol. 28, pp. 43-49.

* cited by examiner

*Primary Examiner* — Marc S Zimmer
(74) *Attorney, Agent, or Firm* — Robert M. Lanning

(57) ABSTRACT

A composition comprises an adduct produced by reacting an amine compound and a cyclic siloxane compound. The amine compound comprises two or more amine groups independently selected from the group consisting of primary amine groups and secondary amine groups. The cyclic siloxane compound comprises two or more first siloxane moieties that contain cyclic ether moieties. An epoxy composition is made by reacting an epoxy resin and the composition comprising the adduct.

19 Claims, No Drawings

ADDUCT OF AN AMINE AND A CYCLIC SILOXANE COMPOUND

CROSS REFERENCE TO RELATED APPLICATIONS

This application claims, pursuant to 35 U.S.C. § 119(e)(1), priority to and the benefit of the filing date of U.S. Patent Application No. 62/257,471 filed on Nov. 19, 2015 which application is hereby incorporated by reference in its entirety.

TECHNICAL FIELD OF THE INVENTION

This application relates to compounds, specifically adducts, made by reacting an amine compound and a cyclic siloxane compound. The application also relates to epoxy compositions made using such adducts.

BACKGROUND

Siloxane compounds are well known for their thermal stability, ability to maintain flexibility at low temperatures, and ability to impart hydrophobicity to surfaces. Therefore, it is not surprising that some have proposed incorporating siloxane compounds into epoxy systems. These solutions have been proposed as a means to reduce brittleness and increase hydrophobicity of the epoxy systems. While such solutions have been proposed, these solutions have not been without their problems. Siloxane compounds generally are not miscible in epoxy resin systems. Therefore, it is possible for a siloxane compound to phase separate from an epoxy system to which it is added. If such phase separation occurs, it can lead to defects in the cured epoxy.

A need therefore remains for siloxane-based compounds that are capable of reacting with epoxy resins and show improved compatibility with or solubility in a range of epoxy systems. A need also remains for epoxy products made by reacting such a siloxane-based compound with an epoxy resin. The invention described herein attempts to meet such needs.

BRIEF SUMMARY OF THE INVENTION

In a first embodiment, the invention provides a composition comprising an adduct produced by reacting an amine compound and a cyclic siloxane compound, wherein (a) the amine compound comprises two or more amine groups independently selected from the group consisting of primary amine groups and secondary amine groups and (b) the cyclic siloxane compound comprises two or more first siloxane moieties, the first siloxane moieties being independently selected from the group consisting of moieties of Formula (I)

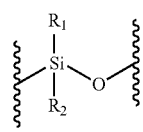

where $R_1$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups, and $R_2$ is a group comprising a cyclic ether moiety.

DETAILED DESCRIPTION OF THE INVENTION

The following definitions are provided to define several of the terms used throughout this application.

As used herein, the term "substituted alkyl groups" refers to univalent functional groups derived from substituted alkanes by removal of a hydrogen atom from a carbon atom of the alkane. In this definition, the term "substituted alkanes" refers to compounds derived from acyclic unbranched and branched hydrocarbons in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom (as in an ether), a nitrogen atom (as in an amine), or a sulfur atom (as in a sulfide).

As used herein, the term "substituted cycloalkyl groups" refers to univalent functional groups derived from substituted cycloalkanes by removal of a hydrogen atom from a carbon atom of the cycloalkane. In this definition, the term "substituted cycloalkanes" refers to compounds derived from saturated monocyclic and polycyclic hydrocarbons (with or without side chains) in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom, a nitrogen atom, or a sulfur atom.

As used herein, the term "alkenyl groups" refers to univalent functional groups derived from acyclic, unbranched and branched olefins (i.e., hydrocarbons having one or more carbon-carbon double bonds) by removal of a hydrogen atom from a carbon atom of the olefin.

As used herein, the term "substituted alkenyl groups" refers to univalent functional groups derived from acyclic, substituted olefins by removal of a hydrogen atom from a carbon atom of the olefin. In this definition, the term "substituted olefins" refers to compounds derived from acyclic, unbranched and branched hydrocarbons having one or more carbon-carbon double bonds in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom (as in an ether) or a sulfur atom (as in a sulfide).

As used herein, the term "cycloalkenyl groups" refers to univalent functional groups derived from cyclic olefins (i.e., non-aromatic, monocyclic and polycyclic hydrocarbons having one or more carbon-carbon double bonds) by removal of a hydrogen atom from a carbon atom of the olefin. The carbon atoms in the cyclic olefins can be substituted with alkyl groups and/or alkenyl groups.

As used herein, the term "substituted cycloalkenyl groups" refers to univalent functional groups derived from substituted cyclic olefins by removal of a hydrogen atom from a carbon atom of the cyclic olefin. In this definition, the term "substituted cyclic olefins" refers to compounds derived from non-aromatic, monocyclic and polycyclic hydrocarbons having one or more carbon-carbon double bonds in which one or more of the hydrogen atoms of the hydrocarbon is replaced with a non-hydrogen atom (e.g., a halogen atom) or a non-alkyl functional group (e.g., hydroxy group, aryl group, heteroaryl group).

As used herein, the term "heterocyclyl groups" refers to univalent functional groups derived from heterocyclic compounds by removal of a hydrogen atom from an atom in the cyclic portion of the heterocyclic compound. In this definition, the term "heterocyclic compounds" refers to compounds derived from non-aromatic, monocyclic and polycyclic compounds having a ring structure composed of atoms of at least two different elements. These heterocyclic compounds can also comprise one or more double bonds.

As used herein, the term "substituted heterocyclyl groups" refers to univalent functional groups derived from substituted heterocyclic compounds by removal of a hydrogen atom from an atom in the cyclic portion of the compound. In this definition, the term "substituted heterocyclic compounds" refers to compounds derived from non-aromatic, monocyclic and polycyclic compounds having a ring structure composed of atoms of at least two different elements where one or more of the hydrogen atoms of the cyclic compound is replaced with a non-hydrogen atom (e.g., a halogen atom) or a functional group (e.g., hydroxy group, alkyl group, aryl group, heteroaryl group). These substituted heterocyclic compounds can also comprise one or more double bonds.

As used herein, the term "substituted aryl groups" refers to univalent functional groups derived from substituted arenes by removal of a hydrogen atom from a ring carbon atom. In this definition, the term "substituted arenes" refers to compounds derived from monocyclic and polycyclic aromatic hydrocarbons in which one or more of the hydrogen atoms of the hydrocarbon is replaced with a non-hydrogen atom (e.g., a halogen atom) or a non-alkyl functional group (e.g., hydroxy group).

As used herein, the term "substituted heteroaryl groups" refers to univalent functional groups derived from substituted heteroarenes by removal of a hydrogen atom from a ring carbon atom. In this definition, the term "substituted arenes" refers to compounds derived from monocyclic and polycyclic aromatic hydrocarbons in which (1) one or more of the hydrogen atoms of the hydrocarbon is replaced with a non-hydrogen atom (e.g., a halogen atom) or a non-alkyl functional group (e.g., hydroxy group) and (2) at least one methine group (—C≡) of the hydrocarbon is replaced by a trivalent heteroatom and/or at least one vinylidene group (—CH═CH—) of the hydrocarbon is replaced by a divalent heteroatom.

As used herein, the term "alkanediyl groups" refers to divalent functional groups derived from alkanes by removal of two hydrogen atoms from the alkane. These hydrogen atoms can be removed from the same carbon atom on the alkane (as in ethane-1,1-diyl) or from different carbon atoms (as in ethane-1,2-diyl).

As used herein, the term "substituted alkanediyl groups" refers to divalent functional groups derived from substituted alkanes by removal of two hydrogen atoms from the alkane. These hydrogen atoms can be removed from the same carbon atom on the substituted alkane (as in 2-fluoroethane-1,1-diyl) or from different carbon atoms (as in 1-fluoroethane-1,2-diyl). In this definition, the term "substituted alkanes" has the same meaning as set forth above in the definition of substituted alkyl groups.

As used herein, the term "alkenediyl groups" refers to divalent functional groups derived from acyclic, unbranched and branched olefins (i.e., hydrocarbons having one or more carbon-carbon double bonds) by removal of two hydrogen atoms from the olefin. These hydrogen atoms can be removed from the same carbon atom on the olefin (as in but-2-ene-1,1-diyl) or from different carbon atoms (as in but-2-ene-1,4-diyl).

As used herein, the term "acyl groups" refers to univalent functional groups derived from alkyl carboxylic acids by removal of a hydroxy group from a carboxylic acid group. In this definition, the term "alkyl carboxylic acids" refers to acyclic, unbranched and branched hydrocarbons having one or more carboxylic acid groups.

As used herein, the term "substituted acyl groups" refers to univalent functional groups derived from substituted alkyl carboxylic acids by removal of a hydroxy group from a carboxylic acid group. In this definition, the term "substituted alkyl carboxylic acids" refers to compounds having one or more carboxylic acid groups bonded to a substituted alkane, and the term "substituted alkane" is defined as it is above in the definition of substituted alkyl groups.

As used herein, the term "siloxy groups" refers to univalent functional groups having the structure —[OSiR$_x$R$_y$]$_w$R$_z$, where R$_x$, R$_y$, and R$_z$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups and the variable w is an integer equal to or greater than 1. In a preferred embodiment, R$_x$, R$_y$, and R$_z$ are independently selected from the group consisting of alkyl groups (e.g., $C_1$-$C_8$ alkyl groups), and the variable w is an integer from 1 to 50, more preferably 1 to 20.

In a first embodiment, the invention provides a composition comprising an adduct produced by reacting at least one amine compound and at least one cyclic siloxane compound. The amine compound comprises primary or secondary amine groups, and the cyclic siloxane compound comprises functional groups that are capable of reacting in an addition reaction with the primary or secondary amine groups present in the amine compound.

The amine compound used in producing the adduct can be any suitable amine compound. Preferably, the amine compound comprises at least two amine groups selected from the group consisting of primary amine groups and secondary amine groups. Suitable amine compounds include, but are not limited to, isophorone diamine, diethylenetriamine, triethylenetetramine, tetraethylenepentamine, diproprenediamine, diethylaminopropylamine, hexamethylenediamine, N-aminoethylpiperazine, 4,4'-methylenebis(cyclohexylamine), 2,2'-Dimethyl-4,4'-methylenebis(cyclohexylamine), 1,8-diamine-p-menthane, xylenediamine (including xylenediamine trimmers), 1,3-bis(aminomethyl)cyclohexane, 1,2-diaminobenzene (metaphenylene diamine), 1,3-bis(aminomethyl)benzene, 4,4'-methylenebisbenzenamine (4,4'-diaminodiphenylmethane), 4,4'-sulfonylbisbenzenamine (4,4'-diaminodiphenyl sulfone), and mixtures thereof. Other suitable amine compounds include the amine curatives described in "Handbook of Epoxy Resins" by Henry Lee and Kris Neville (McGraw Hill Book Company, 1982 reissue), "Protective Coatings Fundamental of Chemistry and Composition" by C. H. Hare (SSPC 1994), and other references. Suitable amine compounds are also commercially sold under the names Aradur® (Huntsman Advanced Materials), Ancamine® (Air Products and Chemicals, Inc.), and EPIKURE (Momentive/Hexion).

As noted above, the cyclic siloxane compound comprises functional groups that are capable of reacting in an addition reaction with the amine groups present in the amine compound. These functional groups can be any suitable group capable of undergoing such a reaction with the amine groups. Preferably, these functional groups are cyclic ethers. Preferably, the cyclic siloxane compound comprises at least two cyclic ether moieties.

In a preferred embodiment, the cyclic siloxane compound comprises two or more first siloxane moieties. The first siloxane moieties are independently selected from the group consisting of moieties conforming to the structure of Formula (I)

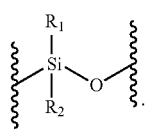
(I)

In the structure of Formula (I), $R_1$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups, and $R_2$ is a group comprising a cyclic ether moiety. As noted above, the first siloxane moieties are independently selected from the recite group. Thus, the first siloxane moieties present in the cyclic siloxane compound can each comprise different substituents selected from the recited groups.

The structure of Formula (IZ) depicts a cyclic siloxane compound containing only first siloxane moieties

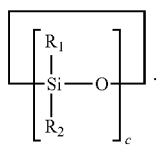
(IZ)

In the structure of Formula (IZ), each $R_1$ and $R_2$ is independently selected from the various groups recited above for the structure of Formula (I). The variable c is a positive integer equal to or greater than 3. Preferably, the variable c is 10 or less, more preferably 8 or less, and most preferably 6 or less.

In another preferred embodiment, the cyclic siloxane compound comprises at least one second siloxane moiety in addition to the first siloxane moieties. The second siloxane moiety preferably is selected from the group consisting of moieties conforming to the structure of Formula (X) below

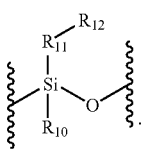
(X)

In the structure of Formula (X), $R_{10}$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups. $R_{11}$ is selected from the group consisting of alkanediyl groups and alkenediyl groups. $R_{12}$ is selected from the group consisting of aryl groups, substituted aryl groups, heteroaryl groups, and substituted heteroaryl groups.

The structure of Formula (IA) below depicts an exemplary structure for a cyclic siloxane compound comprising first and second siloxane moieties as described above. The structure of Formula (IA) is

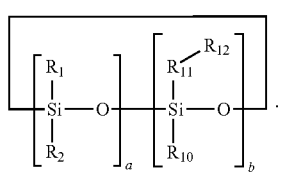
(IA)

In the structure of Formula (IA), each $R_1$, $R_2$, $R_{10}$, $R_{11}$, and $R_{12}$ is independently selected from the same groups recited above for the structures of Formula (I) and Formula (X). The variable a denotes the number of first siloxane moieties present in the cyclic siloxane compound and is selected from the group consisting of positive integers equal to or greater than 2. The variable b denotes the number of second siloxane moieties present in the cyclic siloxane compound and is selected from the group consisting of positive integers equal to or greater than 1. Preferably, the sum of the variables a and b is 3 or more, more preferably 4 or more. In another preferred embodiment, the sum of the variables a and b is 10 or less, more preferably 8 or less, most preferably 6 or less (e.g., 5 or less). For the sake of simplicity, the structure of Formula (IA) depicts the cyclic siloxane compound in a block configuration, with siloxane moieties having the same structure grouped together in the cyclic siloxane compound. The cyclic siloxane can have such a block configuration. However, more commonly, the cyclic siloxane compound will have a random configuration, in which the different siloxane moieties are randomly arranged in each molecule of the cyclic siloxane compound. The structure of Formula (IA) is intended to encompass and serve as a schematic representation of the structure of both types of compounds—the block configuration and the random configuration.

In the structures of Formulae (I), (IA) and (IZ), $R_1$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups. In a preferred embodiment, $R_1$ is selected from the group consisting of alkyl groups, with $C_1$-$C_8$ alkyl groups being particularly preferred. For example, in a preferred embodiment, $R_1$ is a methyl group.

As noted above, in the structures of Formulae (I), (IA) and (IZ), $R_2$ is a group comprising a cyclic ether moiety. The cyclic ether moiety can comprise any suitable number of atoms, such as the three-membered epoxide moiety, a four-membered oxetanyl moiety, a five-membered tetrahydrofuranyl moiety, or a six-membered tetrahydropyranyl moiety. In a preferred embodiment, $R_2$ comprises an epoxide moiety. Further, the $R_2$ group can comprise any suitable linear or cyclic moiety attached to the cyclic ether moiety. For example, the $R_2$ group can comprise an alkanediyl moiety bonded to the cyclic ether moiety, such as in a glycidyl group (2,3-epoxypropyl group). Alternatively, the $R_2$ group can comprise a cyclic moiety forming a fused ring system with the cyclic ether moiety, such as in a 3,4-epoxycyclohexyl group. In a preferred embodiment, $R_2$ is selected from the group consisting of 5,6-epoxyhexyl and 2-(3,4-epoxycyclohexyl)ethyl. In another preferred embodiment, $R_2$ is a group conforming to the structure —$R_5$—O—$R_6$, where $R_5$ is an alkanediyl group and $R_6$ is a group comprising an epoxide moiety. In a preferred embodiment, $R_5$ is a propane-1,3-diyl group, and $R_6$ is a glycidyl group.

In the structures of Formula (X) and (IA), $R_{10}$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups. In a preferred embodiment, $R_{10}$ is selected from the group consisting of alkyl groups, with $C_1$-$C_8$ alkyl groups being particularly preferred. For example, in a preferred embodiment, $R_{10}$ is a methyl group.

In the structures of Formula (X) and (IA), $R_{11}$ is selected from the group consisting of alkanediyl groups and alkenediyl groups. $C_1$-$C_8$ alkanediyl groups and $C_1$-$C_8$ alkenediyl groups are preferred, but other suitable alkanediyl and alkenediyl groups can be present. In a preferred embodiment, $R_{11}$ is a $C_1$-$C_8$ alkanediyl group, one preferred example of which is 2-methylethane-1,2-diyl.

In the structures of Formula (X) and (IA), $R_{12}$ is selected from the group consisting of aryl groups, substituted aryl groups, heteroaryl groups, and substituted heteroaryl groups. In a preferred embodiment, $R_{12}$ is selected from the group consisting of $C_6$-$C_{10}$ aryl groups, one preferred example of which is a phenyl group.

Thus, in a preferred embodiment, $R_1$ is an alkyl group (preferably a $C_1$-$C_8$ alkyl group), and $R_2$ is a group comprising an epoxide moiety. In another preferred embodiment, $R_{10}$ is an alkyl group (preferably a $C_1$-$C_8$ alkyl group), $R_{11}$ is an alkanediyl group (preferably a $C_1$-$C_8$ alkanediyl group), and $R_{12}$ is an aryl group (preferably a $C_6$-$C_{10}$ aryl group). Thus, in one particular preferred embodiment of a compound conforming to the structure of Formula (IA), $R_1$ is an alkyl group (preferably a $C_1$-$C_8$ alkyl group), $R_2$ is a group comprising an epoxide moiety, $R_{10}$ is an alkyl group (preferably a $C_1$-$C_8$ alkyl group), $R_{11}$ is an alkanediyl group (preferably a $C_1$-$C_8$ alkanediyl group), and $R_{12}$ is an aryl group (preferably a $C_6$-$C_{10}$ aryl group). In a more specific preferred embodiment, $R_1$ is a methyl group, $R_2$ is a group conforming to the structure of —$R_5$—O—$R_6$, $R_5$ is a propane-1,3-diylgroup, $R_6$ is a glycidyl group, $R_{10}$ is a methyl group, $R_{11}$ is a 2-methylethane-1,2-diylgroup, and $R_{12}$ is a phenyl group.

The cyclic siloxane compound can contain any suitable ratio of first siloxane moieties (i.e., moieties conforming to the structure of Formula (I)) and second siloxane moieties (i.e., moieties conforming to the structure of Formula (X)). Preferably, the ratio of first siloxane moieties to second siloxane moieties is about 1:9 or more. More preferably, the ratio of first siloxane moieties to second siloxane moieties is about 1:4 or more, about 1:3 or more, about 3:7 or more, about 1:2 or more, about 4:7 or more, about 3:5 or more, about 4:5 or more, or about 1:1 or more. Preferably, the ratio of first siloxane moieties to second siloxane moieties is about 9:1 or less. More preferably, the ratio of first siloxane moieties to second siloxane moieties is about 4:1 or less, about 3:1 or less, about 7:3 or less, about 2:1 or less, about 7:4 or less, or about 5:3 or less. Thus, in a series of preferred embodiments, the ratio of first siloxane moieties to second siloxane moieties is about 1:9 to about 9:1, about 1:4 to about 4:1, about 1:3 to about 3:1, about 3:7 to about 7:3, about 1:2 to about 2:1, about 4:7 to about 7:4, or about 3:5 to about 5:3. In another preferred embodiment, the ratio of first siloxane moieties to second siloxane moieties is about 4:5 to about 7:4, more preferably about 1:1 to about 7:4 (e.g., about 1:1 to about 5:3). The ratios of first siloxane moieties to second siloxane moieties in the cyclic siloxane compounds described above represent averages for the population or collection of molecules of cyclic siloxane compounds used to make the adduct. Thus, individual molecules used in making the adduct may possess ratios of first and second siloxane moieties falling outside of these ratios. However, when the ratios for such individual molecules are averaged with the ratios for all of the other molecules used in making the adduct, the average ratio for the entire population or collection of molecules used in making the adduct preferably falls within one of the ranges described above.

The cyclic siloxane compounds used in making the adduct can contain any suitable number of siloxane moieties. Generally, the cyclic siloxane compounds comprise three or more siloxane moieties. In a preferred embodiment, about 90% or more of the cyclic siloxane compounds present in the composition contain four siloxane moieties or five siloxane moieties.

In certain embodiments, the cyclic siloxane compounds present in the composition can comprise siloxane moieties other than the first and second siloxane moieties described above. For example, the cyclic siloxane compound can comprise at least one siloxane moiety conforming to the structure of Formula (V) below

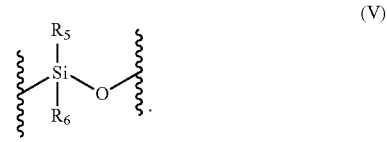

(V)

In the structure of Formula (V), $R_5$ and $R_6$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups. In a preferred embodiment, $R_5$ and $R_6$ are selected from the group consisting of alkyl groups, with $C_1$-$C_{20}$ alkyl groups being particularly preferred. For example, in a preferred embodiment, one $R_5$ and $R_6$ is a $C_1$-$C_8$ alkyl group, preferably a methyl group, and one of $R_5$ and $R_6$ is a $C_{10}$-$C_{20}$ alkyl group (e.g., a $C_{12}$ alkyl group). When the cyclic siloxane compound contains a siloxane moiety conforming to the structure of Formula (V), the total number of siloxane moieties in the cyclic siloxane compound still preferably falls within one of the ranges described above.

The reaction mixture used to produce the adduct can contain other siloxane compounds in addition to those described above. For example, the cyclic siloxane compound can be present in a siloxane composition that comprises a mixture of different siloxane compounds. In such an embodiment, the other siloxane compounds present in the siloxane composition can be either cyclic siloxane compounds or acyclic siloxane compounds.

For example, the siloxane composition can comprise a cyclic siloxane compound containing only second siloxane moieties. Such a cyclic siloxane compound will conform to the structure of Formula (XA) below:

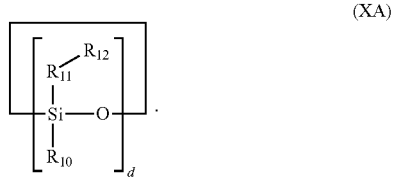

In the structure of Formula (XA), each $R_{10}$, $R_{11}$, and $R_{12}$ is independently selected from the various groups recited above for the structure of Formula (X). The variable d is a positive integer equal to or greater than 3. Preferably, the variable d is 10 or less, more preferably 8 or less, and most preferably 6 or less.

Preferably, the siloxane composition does not contain an excessive amount of cyclic siloxane compounds comprising only second siloxane moieties. In a preferred embodiment, about 10% or less of the cyclic siloxane compounds present in the siloxane composition contain only second siloxane moieties. In other words, in such preferred embodiment, about 10% or less, of the cyclic siloxane compounds present in the siloxane composition conform to the structure of Formula (XA).

In a preferred embodiment, the siloxane composition comprises one or more acyclic siloxane compounds conforming to the structure of Formula (L) below

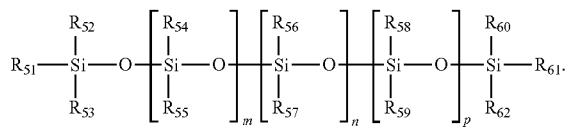

In the structure of Formula (L), $R_{51}$, $R_{52}$, $R_{53}$, $R_{54}$, $R_{55}$, $R_{56}$, $R_{57}$, $R_{58}$, $R_{59}$, $R_{60}$, $R_{61}$, and $R_{62}$ are independently selected from the group consisting of alkyl groups, siloxy groups, and $R_2$. The group $R_2$ is the same as and is discussed in connection with the structure of Formula (I) above. More preferably, $R_{51}$, $R_{52}$, $R_{53}$, $R_{60}$, $R_{61}$, and $R_{62}$ are independently selected from the group consisting of alkyl groups, and $R_{54}$, $R_{55}$, $R_{56}$, $R_{57}$, $R_{58}$, and $R_{59}$ are independently selected from the group consisting of alkyl groups, siloxy groups, and $R_2$. Preferably, the alkyl groups are selected from the group consisting of $C_1$-$C_8$ alkyl groups, more preferably $C_1$-$C_4$ alkyl groups, and most preferably methyl groups. Preferably, the siloxy groups are trimethylsiloxy groups. The variables m, n, and p are independently selected from the group consisting of integers from 0 to 5, more preferably integers from 0 to 3. The sum of the variables m, n, and p preferably is from 1 to 5, more preferably from 1 to 3. Preferably, at least one of $R_{51}$, $R_{52}$, $R_{53}$, $R_{54}$, $R_{55}$, $R_{56}$, $R_{57}$, $R_{58}$, $R_{59}$, $R_{60}$, $R_{61}$, and $R_{62}$ is an $R_2$ group. More preferably, at least one of $R_{54}$, $R_{55}$, $R_{56}$, $R_{57}$, $R_{58}$, and $R_{59}$ is an $R_2$ group. In such an embodiment, the remaining groups preferably are alkyl groups, more preferably methyl groups.

If present in the composition, the acyclic siloxane compound(s) can be present in the siloxane composition in any suitable amount. While not wishing to be bound to any particular theory, it is believed that the presence of the acyclic siloxane compound(s) helps to control the viscosity of the siloxane composition, making it suitable for handling and incorporation with the amine compound to produce the adduct. Accordingly, the amount of acyclic siloxane compound(s) present in the siloxane composition can depend, at least in part, on the desired viscosity of the siloxane composition. Preferably, the acyclic siloxane compounds(s) are present in the siloxane composition in an amount of about 1% or more of the molar amount of cyclic siloxane compounds present in the siloxane composition. In another preferred embodiment, the acyclic siloxane compound(s) are present in the siloxane composition in an amount of about 5% or more, about 6% or more, about 7% or more, or about 8% or more of the molar amount of cyclic siloxane compounds present in the siloxane composition. Preferably, the acyclic siloxane compound(s) are present in the siloxane composition in an amount of about 20% or less of the molar amount of cyclic siloxane compounds present in the siloxane composition.

The cyclic siloxane compounds and compositions described above and used in making the adduct can be produced by any suitable method or process. In one method, the cyclic siloxane compounds and compositions are produced through the hydrosilylation of cyclic hydrosiloxanes with compounds comprising an acyclic, unsaturated carbon-carbon bond, such as an alkene or an alkyne.

In the hydrosilylation reaction described above, the cyclic hydrosiloxane compound comprises at least one siloxane moiety conforming to the structure of Formula (XX) below

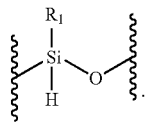

In the structure of Formula (XX), $R_1$ is selected from the groups recited above in the description of the structure of Formula (I). The cyclic hydrosiloxane compound preferably comprises three or more (more preferably, four or more) siloxane moieties conforming to the structure of Formula (XX). The structure of Formula (XXA) below depicts an exemplary structure of such a cyclic hydrosiloxane compound:

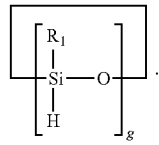

In the structure of Formula (XXA), each $R_1$ is independently selected from the groups recited above in the description of the structure of Formula (I). The variable g represent the number of siloxane moieties in the cyclic hydrosiloxane compound. The variable g is a positive integer equal to or greater than three. In this hydrosilylation reaction, more than one cyclic hydrosiloxane compound can be used. For example, the cyclic hydrosiloxane compound portion of the reactants can be a mixture of several different cyclic hydrosiloxanes comprising moieties conforming to the structure of Formula (XX), such as cyclic hydrotrisiloxanes, cyclic hydrotetrasiloxanes, cyclic hydropentasiloxanes, and cyclic hydrohexasiloxanes. Indeed, commercially available starting materials containing such cyclic hydrosiloxanes often are a mixture of different cyclic hydrosiloxane compounds. In addition, such starting materials can contain small amounts of acyclic hydrosiloxane compounds, but the content of such acyclic hydrosiloxane compounds preferably is relatively low in order to minimize undesirable side reactions and maximize the yield of cyclic siloxane compounds from the hydrosilylation reaction.

As noted above, the cyclic hydrosiloxane compound is reacted with a first compound comprising an acyclic, unsaturated carbon-carbon bond and a second compound comprising an acyclic, unsaturated carbon-carbon bond. The first compound comprising an acyclic, unsaturated carbon-carbon bond reacts with one of the siloxane moieties conforming to the structure of Formula (XX) to form a bond between the silicon atom in the siloxane moiety and a carbon atom in the acyclic, unsaturated carbon-carbon bond. This reaction yields a siloxane moiety conforming to the structure of Formula (X). In other words, the hydrogen in the siloxane moiety reacts with the first compound comprising an acyclic, unsaturated carbon-carbon bond to yield the $—R_{11}—R_{12}$ group in the structure of Formula (X). Thus, the first compound comprising an acyclic, unsaturated carbon-carbon bond can be any suitable alkene or alkyne compound that reacts with the hydrogen in the siloxane moiety to yield an $—R_{11}—R_{12}$ group selected from the groups recited above. The second compound comprising an acyclic, unsaturated carbon-carbon bond reacts with another of the siloxane moieties conforming to the structure of Formula (XX) to form a bond between the silicon atom in the siloxane moiety and a carbon atom in the acyclic, unsaturated carbon-carbon bond. This reaction yields a siloxane moiety conforming to the structure of Formula (I). In other words, the hydrogen in the siloxane moiety reacts with the second compound comprising an acyclic, unsaturated carbon-carbon bond to yield the $R_2$ group in the structure of Formula (I). Thus, the second compound comprising an acyclic, unsaturated carbon-carbon bond can be any suitable alkene or alkyne compound that reacts with the hydrogen in the siloxane moiety to yield an $R_2$ group selected from the groups recited above.

The cyclic hydrosiloxane compound and the compounds containing at least one unsaturated carbon-carbon bond are reacted in a hydrosilylation reaction in the presence of a suitable catalyst, such as a platinum catalyst. A wide variety of hydrosilylation catalysts have been described in the literature. U.S. Pat. No. 6,030,919 (Lewis) generally describes platinum catalysts suitable for use in hydrosilylation reactions. Suitable industrial catalysts include, but are not limited to, Speier's catalyst (chloroplatinic acid in 2-propanol), Ashby's catalyst (a platinum (0)-cyclovinylmethylsiloxane complex), and Karstedt's catalyst (a platinum (0) divinyltetramethyldisiloxane complex). The literature also cites platinum oxide (Nicolas Sabourault at al., *Organic Letters*, 4, 13, p. 2117-2119, (2002)) as well as platinum carbene complexes as effective hydrosilylation catalysts (István E. Markó et al., *Science* 298, p. 204, (2002)). A variety of other metal catalysts such as those containing palladium, rhodium, ruthenium, or iridium are also known to be active for hydrosilylation (M. A. Brook, "Silicon in Organic, Organometallic, and Polymer Chemistry," pp. 401, John Wiley & Sons, 2000). Recent work has also demonstrated that hydrosilylation can be effectively catalyzed by metal complexes of non-noble metals as well (see, e.g., U.S. Pat. No. 9,073,950). In a preferred embodiment, the hydrosilylation catalyst is selected from the group consisting of Ashby's catalyst and Speier's catalyst.

The cyclic hydrosiloxane compound can be reacted with the first and second compounds comprising an acyclic, unsaturated carbon-carbon bond in any suitable order. However, the inventors have found that simultaneous addition of both the first and second compounds can lead to the production of substantial amounts of cyclic siloxane compounds containing only siloxane moieties conforming to the structure of Formula (I) or Formula (X) above. The presence of large amounts of such cyclic siloxane compounds is not desirable because the compound may not exhibit the desired combination of reactivity within an epoxy system (which is provided by the cyclic ether moiety) and compatibility or improved solubility in epoxy resins (which is provided by the $—R_{11}—R_{12}$ group). Thus, in one potential embodiment, the hydrosilylation of the cyclic hydrosiloxane compound is conducted by first slowly adding the first compound comprising an acyclic, unsaturated carbon-carbon bond. The addition of the first compound is then followed by controlled reaction of the resulting intermediate with the second compound comprising an acyclic, unsaturated carbon-carbon bond. For example, the resulting intermediate (produced by reaction the cyclic hydrosiloxane compound and the first compound comprising an acyclic, unsaturated carbon-carbon bond) can be added to a reaction medium containing the second compound comprising an acyclic, unsaturated carbon-carbon bond. Alternatively, the second compound comprising an acyclic, unsaturated carbon-carbon bond can be added to a reaction medium comprising the intermediate (produced by reaction the cyclic hydrosiloxane compound and the first compound comprising an acyclic, unsaturated carbon-carbon bond). This sequential and controlled reaction of the first and second compounds comprising an acyclic, unsaturated carbon-carbon bond has been found to yield a product comprising a relatively high percentage of cyclic siloxane compounds containing a combination of siloxane moieties conforming to the structure of Formula (I) and siloxane moieties conforming to the structure of Formula (X).

In a preferred embodiment of the process, the cyclic hydrosiloxane compound is first reacted with the first compound comprising an acyclic, unsaturated carbon-carbon bond. Following this hydrosilylation reaction, an acyclic hydrosiloxane compound is added to the product produced by the first hydrosilylation reaction. Following the addition of the acyclic hydrosiloxane compound, the resulting mixture of cyclic and linear hydrosiloxane compounds is reacted with the second compound comprising an acyclic, unsaturated carbon-carbon bond. Preferably, this reaction is conducted by slowly adding the mixture of cyclic and linear hydrosiloxane compounds (i.e., the mixture containing the acyclic hydrosiloxane compound and the product of the reaction between the cyclic hydrosiloxane compound and the first compound comprising an acyclic, unsaturated carbon-carbon bond) to a reaction phase containing the second compound comprising an acyclic, unsaturated carbon-carbon bond. As noted above, the reaction of the second compound with the cyclic hydrosiloxane compound yields a siloxane moiety conforming to the structure of Formula (I) in the resulting cyclic siloxane compound. Similarly, the second compound reacts with the acyclic hydrosiloxane compound to yield one or more siloxane moieties containing an $R_2$ group as described above in connection with the structure of Formula (I). The acyclic siloxane compounds conforming to the structure of Formula (L) above are examples of acyclic siloxane compounds produced by such a reaction. While not wishing to be bound to any particular theory, it is believed that an acyclic siloxane compound bearing one or more of such siloxane moieties is desirable because the $R_2$ group will react with the curative(s) used in an epoxy system. When the siloxane compound reacts with the curative, the acyclic siloxane compound will be incorporated into the cured epoxy and will not leach out or be extracted from the cured epoxy.

The acyclic hydrosiloxane compound used in such a reaction can be any suitable acyclic hydrosiloxane compound. Preferably, the acyclic hydrosiloxane compound is selected from the group consisting of compound conforms to the structure of Formula (LXX)

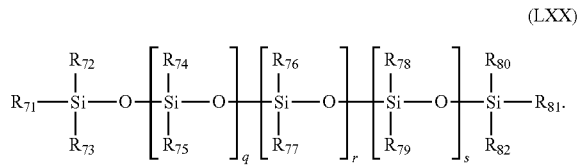

In the structure of Formula (LXX), $R_{71}$, $R_{72}$, $R_{73}$, $R_{74}$, $R_{75}$, $R_{76}$, $R_{77}$, $R_{78}$, $R_{79}$, $R_{80}$, $R_{81}$, and $R_{82}$ are independently selected from the group consisting of hydrogen, alkyl groups, and siloxy groups. More preferably, $R_{71}$, $R_{72}$, $R_{73}$, $R_{70}$, $R_{71}$, and $R_{72}$ are independently selected from the group consisting of alkyl groups, and $R_{74}$, $R_{75}$, $R_{76}$, $R_{77}$, $R_{78}$, and $R_{79}$ are independently selected from the group consisting of hydrogen, alkyl groups, and siloxy groups. Preferably, the alkyl groups are selected from the group consisting of $C_1$-$C_8$ alkyl groups, more preferably $C_1$-$C_4$ alkyl groups, and most preferably methyl groups. Preferably, the siloxy groups are trimethylsiloxy groups. The variables q, r, and s are independently selected from the group consisting of integers from 0 to 5, more preferably integers from 0 to 3. The sum of the variables q, r, and s preferably is from 1 to 5, more preferably from 1 to 3. Preferably, at least one of $R_{71}$, $R_{72}$, $R_{73}$, $R_{74}$, $R_{75}$, $R_{76}$, $R_{77}$, $R_{78}$, $R_{79}$, $R_{80}$, $R_{81}$, and $R_{82}$ is a hydrogen. More preferably, at least one of $R_{74}$, $R_{75}$, $R_{76}$, $R_{77}$, $R_{78}$, and $R_{79}$ is a hydrogen. In such an embodiment, the remaining groups preferably are alkyl groups, more preferably methyl groups.

The amine compound and the cyclic siloxane compound (or the siloxane composition comprising the cyclic siloxane compound) can be reacted in any suitable relative amounts to produce the composition comprising the adduct. Preferably, the amine compound and the cyclic siloxane compound are reacted together with a stoichiometric excess of the amine compound. Within the context of the invention, it is convenient to express the relative amounts of the amine compound and the cyclic siloxane compound (or the siloxane composition containing the cyclic siloxane compound) in terms of amine hydrogen equivalents and epoxy equivalents, respectively. Preferably, the amine compound and the cyclic siloxane compound are reacted together in amounts such that the ratio of amine hydrogen equivalents of the amine compound to epoxy equivalents of the cyclic siloxane compound is about 3:1 or more. More preferably, the ratio of amine hydrogen equivalents of the amine compound to epoxy equivalents of the cyclic siloxane compound is about 4:1 or more, about 6:1 or more, about 8:1 or more, or about 10:1 or more. When the cyclic siloxane compound is present in a siloxane composition comprising additional siloxane compounds, this ratio preferably is calculated using the total epoxy equivalents from all of the siloxane compounds present in the siloxane composition (i.e., the ratio is the ratio of amine hydrogen equivalents of the amine compound to total epoxy equivalents of the siloxane composition).

The adduct and composition (i.e., the composition comprising the adduct) of the invention are believed to be particularly useful in the production of epoxy compositions. The cyclic siloxane compound used in the production of the adduct can improve the flexibility of an epoxy composition relative to a similar epoxy system produced without cyclic siloxane compound(s), and the cyclic siloxane compound can increase the water resistance and thermal stability of the cured epoxy relative to a similar epoxy formulated without the cyclic siloxane compound. However, such cyclic siloxane compounds can exhibit poor solubility or compatibility within certain epoxy resins. The lack of solubility or compatibility can cause such cyclic siloxane compounds to phase separate from the epoxy resin and form a discontinuous phase within the epoxy system. This phase separation of the cyclic siloxane compound can negatively affect the physical appearance of the epoxy composition (i.e., the cured epoxy can exhibit a hazy or milky appearance) and can also negatively affect the physical properties of the epoxy composition due to poor dispersion and/or incomplete reaction of the cyclic siloxane compound into the cured epoxy composition. However, the inventors surprisingly found that reacting such cyclic siloxane compounds with an amine compound to form an adduct can facilitate the incorporation of such cyclic siloxane compounds into an epoxy composition. In particular, the inventors found that adding the adduct/composition of the invention to an epoxy resin can substantially improve the visual appearance of the epoxy composition (i.e., reducing or eliminating the hazy or milky appearance of the epoxy that would otherwise result from the direct addition of the cyclic siloxane compound and amine compound to epoxy resin).

Thus, in a second embodiment, the invention provides an epoxy composition produced by reacting an epoxy resin with the composition of the first embodiment (i.e., the composition comprising the adduct of an amine compound and a cyclic siloxane compound). The composition reacted with the epoxy resin can be any of the compositions (containing any of the adducts) described above in connection with the first embodiment of the invention.

Any suitable epoxy resin can be used to produce the above-described epoxy resin compositions. Suitable epoxy resins are described in "Handbook of Epoxy Resins" by Henry Lee and Kris Neville (McGraw Hill Book Company, 1982 reissue), "Protective Coatings Fundamental of Chemistry and Composition" by C. H. Hare (SSPC 1994), and other references. Suitable epoxy resins include, but are not limited to, bisphenol epoxy resins, novolac epoxy resins, glycidyl epoxy resins (e.g., aliphatic glycidyl ethers and ester and cycloaliphatic glycidyl ethers), cycloaliphatic epoxides, glycidylamine epoxy resins, and mixtures thereof. In a preferred embodiment, the epoxy resin is selected from the group consisting of bisphenol epoxy resins, novolac epoxy resins, glycidyl epoxy resins, cycloaliphatic epoxides, glycidylamine epoxy resins, and mixtures thereof.

Specific examples of epoxy resins suitable for use in the invention include multifunctional phenol novolak epoxy resins (synthesized by reacting phenol novolak with epichlorohydrin,) cresol novolak epoxy resins, and bisphenol A novolak epoxy resins. Examples of commercially available multifunctional glycidyl ether epoxy resins include those epoxy resins having the tradenames Epon 1050, Epon 160, Epon 164, Epon 1031, Epon SU-2.5, Epon SU-3, and Epon SU-8, available from Hexion Specialty Chemicals (Columbus, Ohio). Examples of commercially available multifunctional glycidyl ether epoxy resins also include the "DEN" series of epoxy resins available from Dow Chemical Co. (Midland, Mich.).

Bisphenol epoxy resins suitable for use in the composition include, but are not limited to, those conforming to the structure of Formula (CCC)

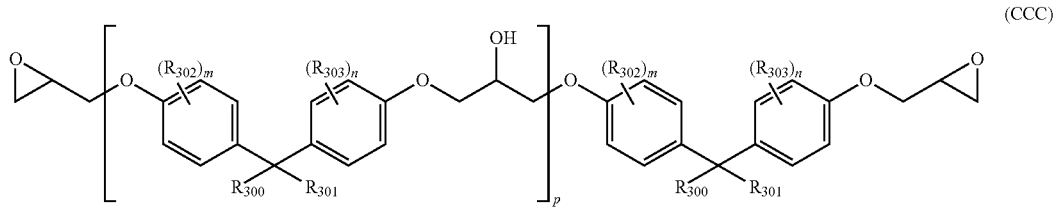
(CCC)

In the structure of Formula (CCC), $R_{300}$ and $R_{301}$ are independently selected from the group consisting of hydrogen, alkyl groups, haloalkyl groups, and aryl groups. $R_{102}$ and $R_{103}$ are independently selected from the group consisting of halogen, alkyl groups, and aryl groups. The variables m and n are independently selected from the group consisting of 0, 1, and 2; and the variable p is selected from the group consisting of 0 and integers from 1 to 50, more preferably 0 and integers from 1 to 25. Suitable commercial examples of these epoxy resins are available from Momentive (formely Hexion) under the tradename "Epon", The Dow Chemical Company (tradename "D.E.R."), and Huntsman Corporation's Advanced Materials business unit (tradename "Araldite"). Examples of suitable epoxy resins that are diglycidyl ethers of bisphenol A include, but are not limited to, those having the trade designations: Epon Resins 825, 826, and 828 (available from Hexion Specialty Chemicals); D.E.R. 330, 331, and 332 resins (available from Dow Chemical Co.); and Araldite GY 6008, GY 6010, and GY 2600 resins (available from Ciba Specialty Chemicals, Tarrytown, N.Y.). Examples of suitable epoxy resins that are diglycidyl ethers of bisphenol F include, but are not limited to, those having the trade designations: EPON Resin 862 resin (available from Hexion Specialty Chemicals); and Araldite GY 281, GY 282, GY 285, PY 306, and PY 307 resins (available from Ciba Specialty Chemicals).

Novolac epoxy resins suitable for use in the composition include, but are not limited to, those conforming to the structure of Formula (CCCX)

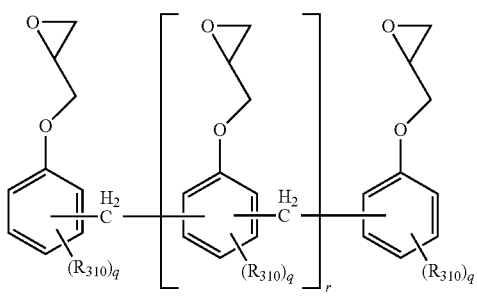
(CCCX)

In the structure of Formula (CCCX), $R_{310}$ is selected from the group consisting of halogen, alkyl groups, haloalkyl groups, and aryl groups. The variable q is selected from the group consisting of 0, 1, and 2; and the variable r is selected from the group consisting of integers from 0 to 50, more preferably integers from 0 to 25. Suitable commercial examples of these resins are available from The Dow Chemical Company under the tradename "D.E.N.™," and Huntsman Corporation's Advanced Materials business unit under the tradename "Araldite."

Suitable epoxy resins also include those derived from the poly-addition of dicyclopentadiene and phenol, which epoxy resins conform to the structure of Formula (CCCXV)

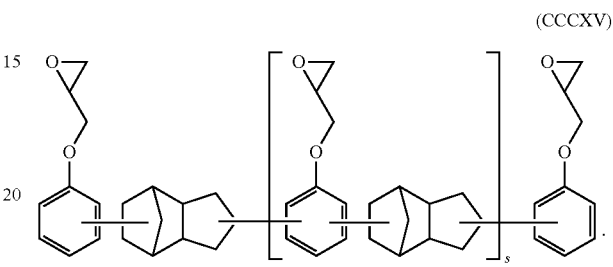
(CCCXV)

In the structure of Formula (CCCXV), the variable s is selected from the group consisting of integers from 0 to 50, more preferably integers from 0 to 25. Suitable commercial examples of these resins are available from Huntsman Chemical (East Lansing, Mich.) under the tradename "Tactix," such as the Tactix 756 and Tactix 556 epoxy resins.

Cycloaliphatic glycidyl ether epoxy resins suitable for use in the composition include, but are not limited to, those conforming to the structure of Formula (CCCXX)

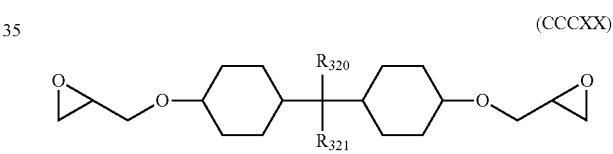
(CCCXX)

In the structure of Formula (CCCXX), $R_{320}$ and $R_{321}$ are independently selected from the group consisting of hydrogen, alkyl groups, haloalkyl groups, and aryl groups. Suitable commercial examples of these materials are believed to be available from CVC Thermoset Specialties under the tradename "Epalloy™," from New Japan Chemical Company, Ltd. under the tradename "Rikaresin HBE-100," and from Adeka USA Corporation under the tradename "Adeka Resin 4080."

Further examples of epoxy resins suitable for use in the epoxy compositions of the invention include glycidyl amine epoxy resins. Suitable examples of glycidyl amine epoxy resins include, but are not limited to, triglycidyl-p-aminophenol (also known as 4-glycidyloxy-N,N-diglycidylaniline), N,N,N,N-tetraglycidyl-4,4-methylenebis benzylamine (also known as 4,4'-Methylenebis(N,N-diglycidylaniline)), and N,N,N',N'-tetraglycidyl-m-xylenediamine. Suitable commercial examples of glycidyl amine epoxy resins include, but are not limited to, the ERISYS™ GE resins available from CVC Thermoset Specialties and the TETRAD® X resins available from Mitsubishi Gas Chemical Company, Inc.

The epoxy resin can have any suitable epoxy equivalent weight. Preferably, the epoxy resin has an epoxy equivalent weight of about 170 g/eq. to about 500 g/eq., about 170 g/eq. to about 350 g/eq., or about 170 g/eq. to about 250 g/eq. The epoxy resin can have an average functionality of from about 1.5 to about 10.

To produce the epoxy composition, the epoxy resin and the composition comprising the adduct can be combined in any suitable amounts. Typically, the epoxy resin and the composition are reacted together in amounts such that the ratio of total epoxy equivalents (from both the epoxy resin as well as the epoxy-containing siloxane compounds used in producing the adduct) to amine hydrogen equivalents (from the amine compound used in producing the adduct) is about 1:2 to about 5:1. Preferably, the ratio of total epoxy equivalents to total amine hydrogen equivalents is about 1:2 to about 2:1, more preferably about 2:3 to about 3:2, and most preferably about 1:1.

The epoxy compositions of the invention can be used in a variety of applications. For example, such epoxies can be used as paints and coatings, such as thermally insulative coatings, corrosion prevention coatings, high temperature resistant coatings, chemical resistant coatings, release coatings, release liners, anti-fouling coatings for surfaces that come into contact with water (e.g., seawater), anti-abrasion coatings, and flexible waterproof coatings for fabrics, wood, paper, and the like. Such epoxies can also be used in bulk applications where waterproofing, flexibility, and/or improved toughness are desired. Suitable bulk applications for the epoxies include, but are not limited to, encapsulants, embedding resins, conformal coatings for electronics, waterproof coatings or potting for electrical equipment or electrical insulators, sound dampening materials, foamed epoxies (such as those used in insulation, cushioning, sound dampening, and syntactic foam), cast or molded epoxy parts, filled epoxies (e.g., epoxies filled with glass fibers or glass microspheres), and epoxy-based circuit boards. Epoxies made using the composition and/or cyclic siloxane compound of the invention can also be used in adhesives. Such epoxy adhesives can be used in wood, plastic, and/or metal laminates, attaching circuit elements to circuit boards, and other applications in which epoxy-based adhesives typically are used.

The following examples further illustrate the subject matter described above but, of course, should not be construed as in any way limiting the scope thereof.

EXAMPLE 1

This example demonstrates the production of a composition comprising an adduct according to the invention.

Approximately 5.69 g of 1,3,5,7-tetrakis(2,1-ethanediyl-3,4-epoxycyclohexyl)-1,3,5,7-tetramethylcyclotetrasiloxane (CAS No. 121225-98-7) (0.0077 moles, 0.0309 epoxy equivalents) was blended with 14.50 grams (0.085 moles, 0.341 amine hydrogen equivalents) of isophorone diamine (Aldrich, mixed isomers) and 0.24 g of phenol (added as an accelerator). The resulting mixture was heated at a temperature of approximately 80° C. for approximately 20 hours. The resulting transparent amber-yellow colored liquid ("Adduct 1") was modestly increased in viscosity over the original mixture. The 1,3,5,7-tetrakis(2,1-ethanediyl-3,4-epoxycyclohexyl)-1,3,5,7-tetramethylcyclotetrasiloxane was not soluble in methanol, but Adduct 1 was completely soluble in methanol and immediately formed a transparent solution upon addition to the methanol.

A sample of Adduct 1 was dissolved in methanol and approximately 0.1% (v/v) of formic acid was added. The resulting solution was analyzed using liquid chromatography-mass spectrometry (LC-MS) and direct electron spray ionization to characterize the different molecular species present in Adduct 1. The mobile phase used in the LC-MS analysis consisted of methanol and water. The gradient and flow rate of the mobile phase is set forth on Table 1 below.

TABLE 1

Composition and flow rate of the mobile phase used in the LC-MS analysis.

| Time (minutes) | Flow Rate (mL/min) | Vol. % Methanol | Vol. % Water |
|---|---|---|---|
| Initial | 0.400 | 20 | 80 |
| 0.80 | 0.400 | 20 | 80 |
| 15.00 | 0.400 | 95 | 5 |
| 20.00 | 0.400 | 95 | 5 |
| 20.10 | 0.400 | 20 | 80 |
| 24.00 | 0.400 | 20 | 80 |

The mass peaks obtained from the LC-MS analysis showed that Adduct 1 contained adducts formed by the reaction of the cyclic siloxane compound and the amine compound. For example, a strong peak was observed at a mass of 1463, which was interpreted as the tetra adduct (i.e., four isophorone diamine molecules reacted with one molecule of the cyclic siloxane compound, which would have an expected mass of 1418) paired with a formate ion. Strong peaks were also observed at masses which would correspond with adducts resulting from the reaction of 2 or 3 isophorone diamine molecules with one molecule of the cyclic siloxane compound.

EXAMPLE 2

This example demonstrates the production of a composition comprising an adduct according to the invention and the use of such composition in the production of epoxy compositions.

Approximately 114.52 g of 4,4'-methylenebis(cyclohexylamine) ("PACM") was combined with approximately 54.53 g of a siloxane composition. The siloxane composition comprised a mixture of cyclic siloxane compounds and acyclic siloxane compounds. The majority of the cyclic siloxane compounds present in the composition contained four or five siloxane moieties. Further, a majority of the cyclic siloxane compounds present in the composition contained at least two siloxane moieties conforming to the structure of Formula (I) in which $R_1$ is methyl, $R_2$ is —$R_5$—O—$R_6$, $R_5$ is propane-1,3-diylgroup, and $R_6$ is glycidyl. Once combined, the PACM and the siloxane composition were mixed for 24 hours and allowed to react to form an adduct ("Adduct 2"). The ratio of amine hydrogen equivalents (from the PACM) to epoxy equivalents (from the siloxane composition) was approximately 12.14:1.

The resulting adduct was mixed with several epoxy resins and cured at a temperature of approximately 70° C. for approximately 16 hours to produce cured epoxy compositions (Samples 2A-2C). The formulation used to produce each of these epoxy compositions is listed in Table 2 below.

TABLE 2

Formulations for Samples 2A-2C.

| Sample | Amount of Adduct 2 | Amount of additional PACM | Resin | Amount of resin | Visual appearance after cure |
|---|---|---|---|---|---|
| 2A | 45.07 g | 0 g | Epon 828 | 100.03 g | Clear |
| 2B | 23.25 g | 1.12 g | Epalloy 8240 | 50.63 g | Clear |
| 2C | 23.25 g | 0.78 g | Epalloy 8280 | 50.97 g | Clear |

For purposes of comparison, cured epoxy compositions were also made by adding the same relative amounts of PACM and the cyclic siloxane composition to the epoxy resins (Comparative Samples ("C.S.") 2A-2C). The formulation used to produce each of these epoxy compositions is listed in Table 3 below.

TABLE 3

Formulations for Comparative Samples 2A-2C.

| Sample | Amount of siloxane composition | Amount of PACM | Resin | Amount of resin | Visual appearance after cure |
|---|---|---|---|---|---|
| C.S. 2A | 15.00 g | 31.57 g | Epon 828 | 103.46 g | Translucent |
| C.S. 2B | 7.50 g | 16.87 g | Epalloy 8240 | 50.63 g | Opaque |
| C.S. 2C | 7.50 g | 16.53 g | Epalloy 8280 | 50.97 g | Opaque |

As can be seen from a comparison of the data in Tables 2 and 3, the epoxy compositions produced with the adduct of the invention exhibited vastly improved visual appearance compared to the epoxy compositions produced by direct addition of the PACM and the cyclic siloxane composition. Not only does this improved visual appearance make these cured epoxy compositions suitable for use in a wider variety of applications, it is also an indicator that the cyclic siloxane composition is better dispersed and incorporated into the cured epoxy composition. This improved dispersion and incorporation should mean that the inventive epoxy compositions (Samples 2A-2C) exhibit improved physical properties relative to the comparative epoxy compositions.

EXAMPLE 3

This example demonstrates the production of a composition comprising an adduct according to the invention and the use of such composition in the production of epoxy compositions.

Approximately 114.52 g of 1,3-bis(aminomethyl)benzene ("MXDA") was combined with approximately 50 g of the same siloxane composition used in Example 2. Once combined, the MXDA and the siloxane composition were mixed for 24 hours and allowed to react to form an adduct ("Adduct 3"). The ratio of amine hydrogen equivalents (from the MXDA) to epoxy equivalents (from the siloxane composition) was approximately 8.82:1.

The resulting adduct was mixed with several epoxy resins and cured at a temperature of approximately 70° C. for approximately 16 hours to produce cured epoxy compositions (Samples 3A-3D). The formulation used to produce each of these epoxy compositions is listed in Table 4 below.

TABLE 4

Formulations for Samples 3A-3D.

| Sample | Amount of Adduct 3 | Amount of additional MXDA | Resin | Amount of resin | Visual appearance after cure |
|---|---|---|---|---|---|
| 3A | 2.95 g | 0 g | Epon 828 | 7.04 g | Clear |
| 3B | 2.60 g | 0 g | Epalloy 8240 | 7.41 g | Clear |
| 3C | 3.05 g | 0 g | Epalloy 8280 | 6.94 g | Clear |
| 3D | 3.03 g | 0 g | Epalloy 8280 | 6.97 g | Hazy |

For purposes of comparison, a cured epoxy composition was also made by adding similar relative amounts of MXDA and the cyclic siloxane composition to an epoxy resin (Comparative Sample ("C.S.") 3A). The formulation used to produce this epoxy composition is listed in Table 5 below.

TABLE 5

Formulation for Comparative Sample 3A.

| Sample | Amount of siloxane composition | Amount of MXDA | Resin | Amount of resin | Visual appearance after cure |
|---|---|---|---|---|---|
| C.S. 3A | 1.50 g | 1.48 g | Epon 828 | 7.03 g | Opaque |

As can be seen from a comparison of the data in Tables 4 and 5, the epoxy compositions produced with the adduct of the invention exhibited vastly improved visual appearance compared to the epoxy compositions produced by direct addition of the PACM and the cyclic siloxane composition. Indeed, all of the samples were visually transparent, with only Sample 3D exhibiting a slightly hazy appearance. Not only does this improved visual appearance make these cured epoxy compositions suitable for use in a wider variety of applications, it is also an indicator that the cyclic siloxane composition is better dispersed and incorporated into the cured epoxy composition. This improved dispersion and incorporation should mean that the inventive epoxy compositions (Samples 3A-3D) exhibit improved physical properties relative to the comparative epoxy composition.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A composition comprising an adduct produced by reacting an amine compound and a cyclic siloxane compound, wherein (a) the amine compound comprises two or more amine groups independently selected from the group consisting of primary amine groups and secondary amine groups and (b) the cyclic siloxane compound comprises two or more first siloxane moieties and one or more second siloxane moieties, the first siloxane moieties being independently selected from the group consisting of moieties conforming to the structure of Formula (I)

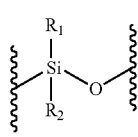
(I)

where $R_1$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups, and $R_2$ is a group comprising a cyclic ether moiety, and the second siloxane moieties being independently selected from the group consisting of moieties of Formula (X)

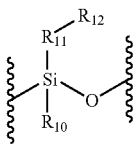
(X)

where $R_{10}$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclic groups, substituted heterocyclic groups, aryl groups, substituted aryl groups, heteroaryl groups, and substituted heteroaryl groups; $R_{11}$ is selected from the group consisting of alkanediyl groups and alkenediyl groups; and $R_{12}$ is selected from the group consisting of aryl groups, substituted aryl groups, heteroaryl groups, and substituted heteroaryl groups.

2. The composition of claim 1, wherein $R_2$ comprises an epoxide moiety.

3. The composition of claim 2, wherein $R_2$ is selected from the group consisting of 5,6-epoxyhexyl and 2-(3,4-epoxycyclohexyl)ethyl.

4. The composition of claim 2, wherein $R_2$ is a group conforming to the structure —$R_5$—O—$R_6$, where $R_5$ is an alkanediyl group and $R_6$ is a group comprising an epoxide moiety.

5. The composition of claim 4, wherein $R_5$ is a propane-1,3-diyl group, and $R_6$ is a glycidyl group.

6. The composition of claim 1, wherein $R_1$ is selected from the group consisting of alkyl groups.

7. The composition of claim 6, wherein $R_1$ is a methyl group.

8. The composition of claim 1, wherein $R_{10}$ is an alkyl group, $R_{11}$ is an alkanediyl group, and $R_{12}$ is an aryl group.

9. The composition of claim 8, wherein $R_{10}$ is a methyl group, $R_{11}$ is a 2-methylethane-1,2-diyl group, and $R_{12}$ is a phenyl group.

10. The composition of claim 1, wherein the cyclic siloxane compound comprises two or more second siloxane moieties.

11. The composition of claim 1, wherein the cyclic siloxane compound comprises four to eight siloxane moieties.

12. An epoxy composition produced by reacting an epoxy resin and the composition of claim 1.

13. An epoxy composition produced by reacting an epoxy resin and a composition comprising an adduct produced by reacting an amine compound and a cyclic siloxane compound, wherein (a) the amine compound comprises two or more amine groups independently selected from the group consisting of primary amine groups and secondary amine groups and (b) the cyclic siloxane compound comprises two or more first siloxane moieties, the first siloxane moieties being independently selected from the group consisting of moieties conforming to the structure of Formula (I)

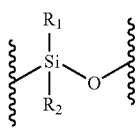
(I)

where $R_1$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups, and $R_2$ is a group comprising a cyclic ether moiety.

14. The epoxy composition of claim 13, wherein $R_2$ comprises an epoxide moiety.

15. The epoxy composition of claim 14, wherein $R_2$ is selected from the group consisting of 5,6-epoxyhexyl and 2-(3,4-epoxycyclohexyl)ethyl.

16. The composition of claim 14, wherein $R_2$ is a group conforming to the structure —$R_5$—O—$R_6$, where $R_5$ is an alkanediyl group and $R_6$ is a group comprising an epoxide moiety.

17. The composition of claim 16, wherein $R_5$ is a propane-1,3-diyl group, and $R_6$ is a glycidyl group.

18. The composition of claim 13, wherein $R_1$ is selected from the group consisting of alkyl groups.

19. The composition of claim 18, wherein $R_1$ is a methyl group.

* * * * *